(12) United States Patent
Abe

(10) Patent No.: US 9,131,905 B2
(45) Date of Patent: Sep. 15, 2015

(54) RADIOGRAPHIC IMAGING CONTROL APPARATUS AND METHOD

(75) Inventor: Masahiro Abe, Yamato (JP)

(73) Assignee: Canon Kabushiki Kaisha, Tokyo (JP)

( * ) Notice: Subject to any disclaimer, the term of this patent is extended or adjusted under 35 U.S.C. 154(b) by 284 days.

(21) Appl. No.: 12/852,392

(22) Filed: Aug. 6, 2010

(65) Prior Publication Data

US 2011/0051896 A1 Mar. 3, 2011

(30) Foreign Application Priority Data

Sep. 2, 2009 (JP) ................................ 2009-202680

(51) Int. Cl.
*A61B 6/00* (2006.01)

(52) U.S. Cl.
CPC . *A61B 6/00* (2013.01); *A61B 6/545* (2013.01); *A61B 6/583* (2013.01)

(58) Field of Classification Search
CPC ........... A61B 6/00; A61B 6/545; A61B 6/583
USPC .................. 378/114–116, 189, 102
See application file for complete search history.

(56) References Cited

U.S. PATENT DOCUMENTS

| | | | |
|---|---|---|---|
| 6,859,521 B2* | 2/2005 | Spahn | 378/117 |
| 8,077,828 B2* | 12/2011 | Aoyama | 378/62 |
| 2004/0066900 A1 | 4/2004 | Motoki | |
| 2005/0169425 A1* | 8/2005 | Takasawa | 378/97 |
| 2007/0165783 A1* | 7/2007 | Tabanjeh | 378/116 |
| 2010/0054417 A1* | 3/2010 | Nishino et al. | 378/98.8 |

FOREIGN PATENT DOCUMENTS

| | | |
|---|---|---|
| JP | 2000350718 A | 12/2000 |
| JP | 2003-210449 A | 7/2003 |
| JP | 2004-073454 A | 3/2004 |
| JP | 2009089723 A | 4/2009 |
| WO | 2008099644 A1 | 8/2008 |

* cited by examiner

*Primary Examiner* — Hoon Song
(74) *Attorney, Agent, or Firm* — Canon USA Inc. IP Division

(57) ABSTRACT

A radiographic imaging apparatus that is connectable to a plurality of radiation sensors includes an information acquisition unit configured to acquire information about a radiographing site and a radiographing posture of a subject based on an instruction from an operator, a sensor drive status management unit configured to manage drive statuses of the plurality of radiation sensors, and a sensor selection unit configured to select a radiation sensor to be used in performing radiographing from the plurality of radiation sensors based on the acquired information and drive statuses of the plurality of radiation sensors.

18 Claims, 9 Drawing Sheets

FIG. 4

| SERIAL NUMBER | MODEL | CONNECTION STATUS | CONNECTION CONFIGURATION | CORRECTION STATUS | CORRECTION DATA |
|---|---|---|---|---|---|
| 12345678 | 50G | ONLINE | WIRED ATTACHABLE/DETACHABLE TYPE | PERFORMED | C:¥Calibration¥12345678.cal |
| 98765432 | 40EG | OFFLINE | WIRED FIXED TYPE | NOT PERFORMED | |
| 22446688 | 40EG | OFFLINE | WIRED FIXED TYPE | PERFORMED | C:¥Calibration¥22446688.cal |
| 11335577 | 50G | ONLINE | WIRED ATTACHABLE/DETACHABLE TYPE | PERFORMED | C:¥Calibration¥11335577.cal |
| 77776666 | 60G | ONLINE | WIRELESS TYPE | PERFORMED | C:¥Calibration¥77776666.cal |
| 99998888 | 60G | OFFLINE | WIRELESS TYPE | NOT PERFORMED | |

401

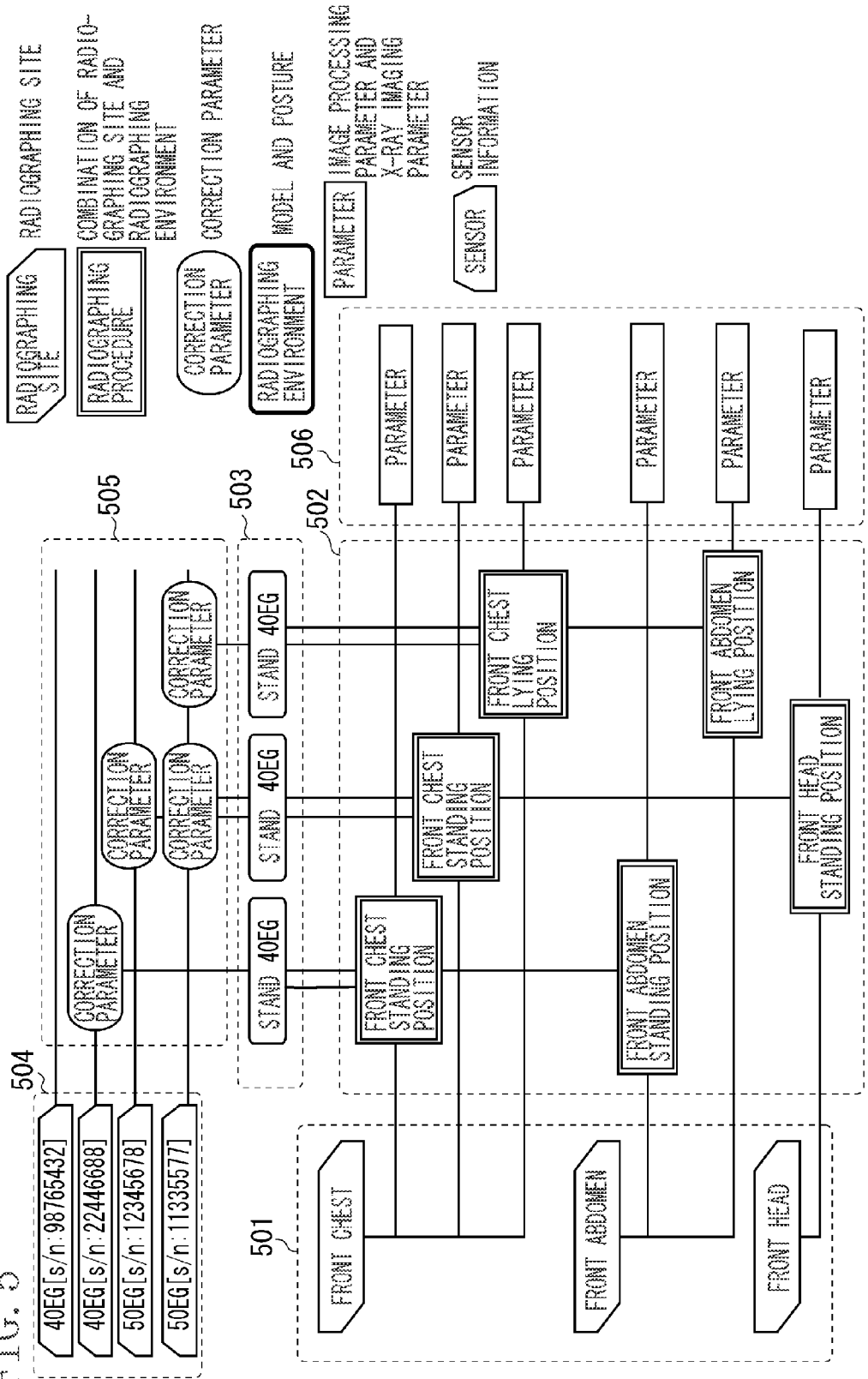

RADIOGRAPHIC IMAGING CONTROL APPARATUS AND METHOD

BACKGROUND OF THE INVENTION

1. Field of the Invention

The present invention relates to a radiographic imaging control apparatus for acquiring a radiographic image for medical use.

2. Description of the Related Art

A radiographic imaging system includes a radiation generation apparatus and a radiographic imaging apparatus having a radiation detection unit, disposed facing each other on opposite sides of a subject. The radiation generation apparatus generates radiation and irradiates the subject, and image information is acquired from signals output from the radiation detection unit. The system is widely used in medical diagnosis and industrial non-destructive inspection.

In a general radiographic imaging system, a plurality of pedestals for each use are often placed in one radiographic imaging room, and radiographing is performed by attaching radiation sensors to the plurality of pedestals. There are various types of pedestals, such as a standing type pedestal in which a patient is radiographed in a standing position, and a table type pedestal in which the patient is radiographed while lying down on his/her back or abdomen.

A cassette-type sensor unit, which is easy to carry, may be detached from the stand type pedestal and then attached to the table type pedestal. Further, one sensor unit can be shared between a plurality of radiographic imaging rooms. Japanese Patent Application Laid-Open No. 2004-73454 discusses a radiographic imaging system which performs radiographing by switching between a plurality of radiation sensors as appropriate.

However, the radiographic imaging system using the plurality of radiation sensors discussed in Japanese Patent Application Laid-Open No. 2004-73454 may impair user-friendliness for an operator. For example, it becomes necessary for the operator to select the radiation sensor to be used in performing radiographing from the plurality of radiation sensors. Further, the radiation sensor includes unique information such as information about a defective pixel, so that it becomes necessary to set a correction parameter to correct such defects for each sensor.

Furthermore, when image processing desired by the operator is to be performed on the acquired radiation image, it becomes necessary to set an image processing parameter. However, since the operator is usually concentrating on a radiographing site and a radiographing posture, it is burdensome for the operator to specify other various settings.

SUMMARY OF THE INVENTION

The present invention is directed to a radiographic imaging control apparatus capable of improving the user-friendliness of a radiographic imaging apparatus that is connectable to a plurality of radiation sensors.

According to an aspect of the present invention, a radiographic imaging apparatus that is connectable to a plurality of radiation sensors includes an information acquisition unit configured to acquire information about a radiographing site and a radiographing posture of a subject based on an instruction from an operator, a sensor drive status management unit configured to manage drive statuses of the plurality of radiation sensors, and a sensor selection unit configured to select a radiation sensor to be used in performing radiographing from the plurality of radiation sensors based on the acquired information and drive statuses of the plurality of radiation sensors.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 4 illustrates an example of a management table according to the first exemplary embodiment of the present invention.

FIG. 5 illustrates an example of a data management structure according to the first exemplary embodiment of the present invention.

DESCRIPTION OF THE EMBODIMENTS

Various exemplary embodiments, features, and aspects of the invention will be described in detail below with reference to the drawings.

Figure 1:
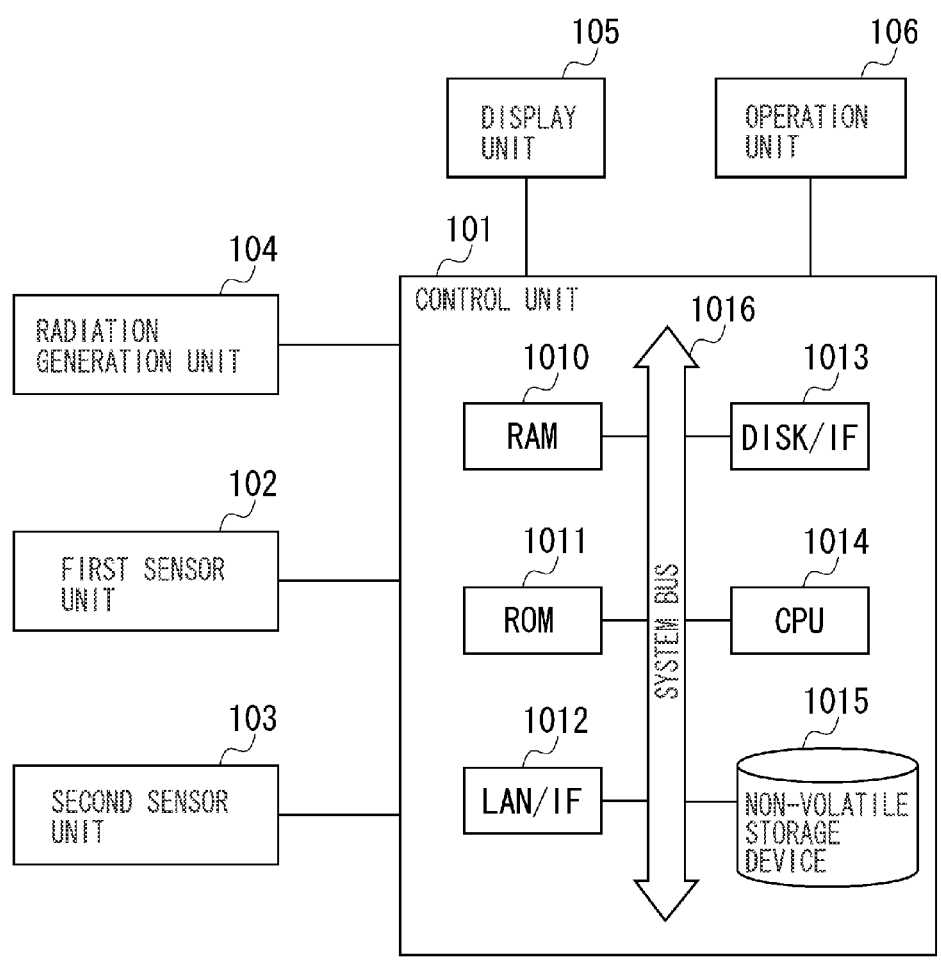
FIG. 1 is a block diagram illustrating a hardware configuration according to a first exemplary embodiment of the present invention.

FIG. 1 illustrates an example of a hardware configuration of a radiographic imaging control system (an X-ray imaging control system) according to a first exemplary embodiment. Referring to FIG. 1, a control unit 101 includes a random access memory (RAM) 1010, a read-only memory 1011, a local area network (LAN) interface (/IF) 1012, a disk/IF 1013, a central processing unit (CPU) 1014, and a non-volatile storage device 1015 such as a hard disk.

The above-described components are connected to each other via a system bus 1016 and has a configuration of a general computer that operates according to a computer program. The control unit 101 controls driving of the sensor unit and a radiation generation unit based on input from the operator.

Further, the control unit 101 uses a database to manage correction data, radiographing conditions, and image data. A display unit 105 is a general monitor such as a cathode-ray tube (CRT) or a liquid crystal display (LCD), which displays the image data and a GUI on a screen.

An operation unit 106, which is configured of input devices such as a mouse, a keyboard, and an irradiation switch, is used by the operator to input various commands and data to the control unit 101.

A radiation generation unit 104 corresponds to the radiation generation apparatus. A first sensor unit 102 and a second sensor unit 103 are sensor units (radiation sensors) that convert radiation signals transmitted through the subject to an image. The captured image is then transferred to the control unit 101.

FIG. 1 illustrates two sensor units (i.e., the first sensor unit 102 and the second sensor unit 103). However, the number of sensor units is not limited to two, and three or more sensor units may be connected to the control unit 101. The control unit 101, and the sensor units 102 and 103, the radiation generation unit 104, the display unit 105, and the operation unit 106 may be connected by wired or wireless connection and may use any communication protocol.

Figure 2:
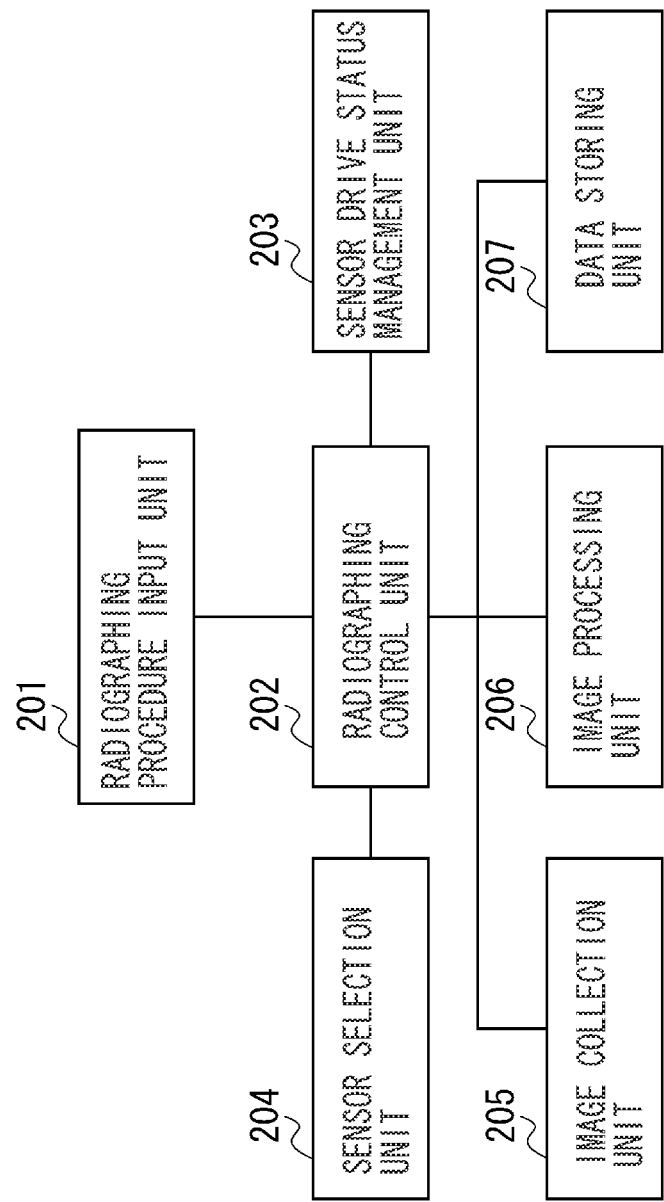
FIG. 2 is a block diagram illustrating a functional configuration according to the first exemplary embodiment of the present invention.

FIG. 2 is a block diagram illustrating a functional configuration according to the present exemplary embodiment. Referring to FIG. 2, a radiographing procedure input unit 201 is used to input a radiographing procedure to be performed. The radiographing procedure according to the present exemplary embodiment will be described below. The actual operation is performed by the operator selecting a radiographing procedure button using the operation unit 106, i.e., the input device such as the mouse or the keyboard.

A radiographing control unit 202 controls radiographing based on the input from the operator. The radiographing control unit 202 performs control of the entire radiographing process, such as drive control of the sensors and management of the progress of radiographing.

A sensor drive status management unit 203 manages the drive status and connection status of each sensor used in the radiographic imaging system. A sensor selection unit 204 determines the sensor to be used in performing radiographing, and the correction parameter. The sensor selection unit 204 determines the sensor and the correction parameter based on radiographing procedure information input from the radiographing procedure input unit 201 and the management status of the sensor drive status management unit 203.

An image collection unit 205 performs radiographing based on an instruction from the radiographing control unit 202. More specifically, upon receiving an irradiation start instruction from a user, the radiation generation apparatus irradiates the subject with radiation. The sensor then receives the radiation transmitted through the subject, and the image collection unit 205 collects the received radiation as the image data. An image processing unit 206 corrects the image data collected by the image collection unit 205 using the correction parameter determined by the sensor selection unit 204.

Further, the image processing unit 206 performs image processing using the image processing parameter determined based on the radiographing procedure information input from by the radiographing procedure input unit 201. A data storing unit 207 stores various data such as the sensor information used by the system, the collected image data, the correction parameters, and the image processing parameters. The various data is managed in the hard disk or the database.

Figure 3:
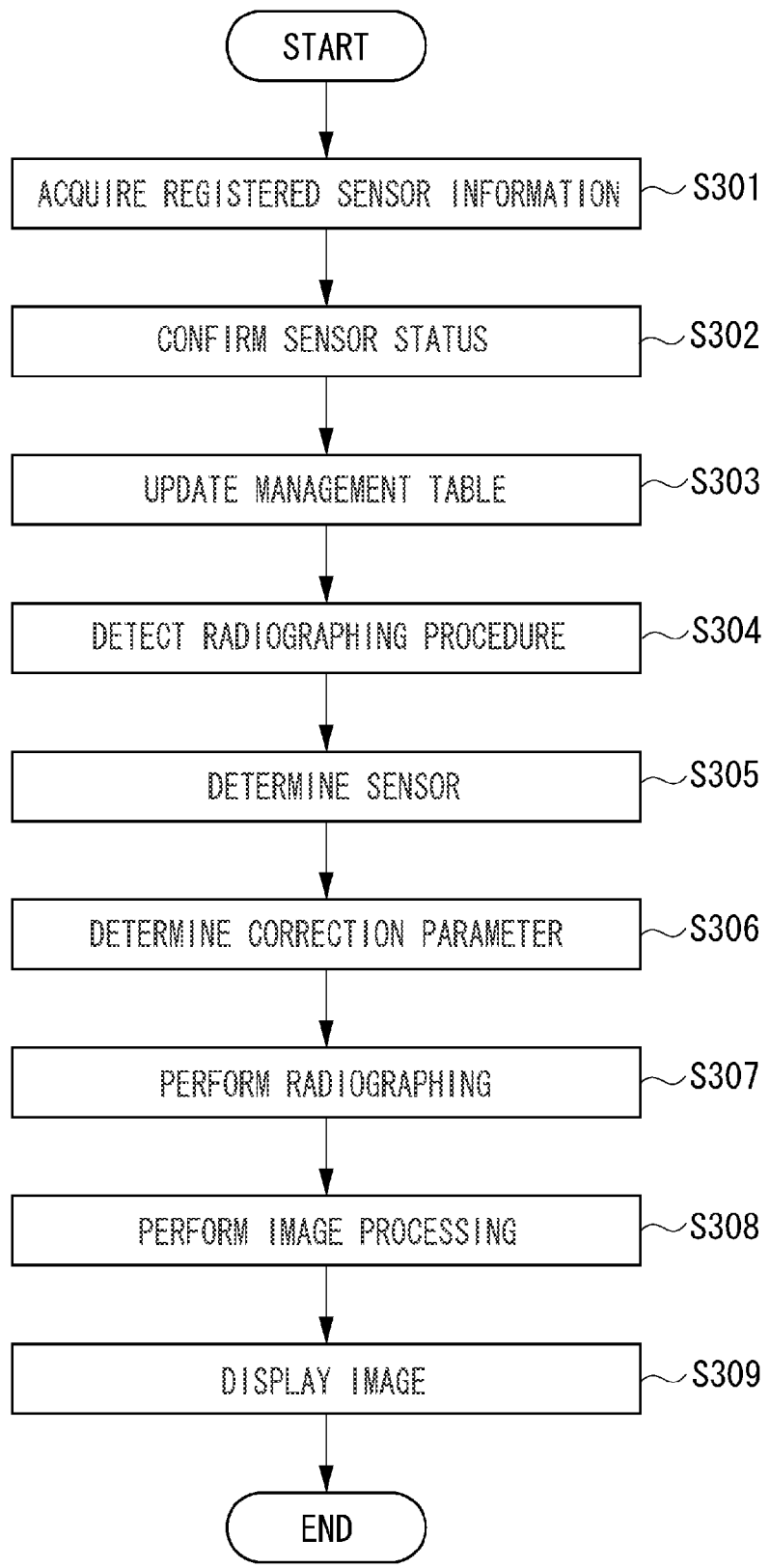
FIG. 3 illustrates a flowchart of a process according to the first exemplary embodiment of the present invention.

FIG. 3 is a flowchart illustrating a process performed by the radiographic imaging system according to the present exemplary embodiment. The process indicates a process flow for performing radiographing, from selecting the radiographing procedure, collecting the image, to displaying the image. The process is executed by each of the hardware configuring the radiographic imaging system.

In step S301, the control unit 101 illustrated in FIG. 1 acquires from the data storing unit 207 the information about the sensor to be used by the radiographic imaging system. The acquired information about the sensor includes a serial number of the sensor, a sensor model for identifying functions of the sensor, a connection configuration of the sensor, communication setting information, and calibration information. Such information is previously registered to the system by an installation personnel, a service personnel, or the user.

In step S302, i.e., a sensor status confirmation step, the control unit 101 confirms the connection status of each sensor unit in the radiographic imaging system using the acquired sensor information. More specifically, the control unit 101 performs a communication trial based on the communication setting of the sensor information, to confirm whether the control unit 101 is communicable with each sensor unit. If communication can be established when the communication trial is performed, the control unit 101 acquires the serial number from the sensor.

The process of step S302 may be performed regularly to confirm the communication status of the sensor unit, or may be performed according to a notification from the sensor unit. The sensor status confirmation step may thus be executed at any timing as long as the radiographic imaging system is in a usable state.

In step S303, the control unit 101 updates a sensor status management table managed by the sensor drive status management unit 203 based on the sensor status confirmed in step S302.

FIG. 4 illustrates an example of a sensor status management table according to the present exemplary embodiment. Referring to FIG. 4, the information managed in the table includes the serial number of the sensor, the sensor model, the connection status, the connection configuration, a correction status, and the correction data.

The serial number of the sensor is an identification number with which each sensor unit can be identified. The model indicates a sensor model, and different sensors of the same model have the same performance and function.

The connection status indicates whether the control unit is communicable with the sensor unit. The correction status indicates whether the sensor unit is performing the correction process. If the sensor unit is performing the correction process, a location of a file in which the correction parameter is written is indicated as the correction data.

In step S304, the control unit 101 detects the radiographing procedure selected and instructed by the operator (i.e., an radiographing procedure detection step). Further, the control unit 101 determines at the same time the image processing parameter and the radiographic imaging parameter based on the selected radiographing procedure. The process then proceeds to step S305.

In step S305, the control unit 101 determines the sensor unit to be used in performing radiographing based on the radiographing procedure information determined in step S304 (i.e., a sensor determination step). The process for determining the sensor from the radiographing procedure information will be described below. Upon the control unit 101 determining the sensor unit in step S305, the process proceeds to step S306.

In step S306, the control unit 101 determines the correction parameter corresponding to the sensor unit determined in step S305. More specifically, the control unit 101 refers to a sensor drive status management table 401 illustrated in FIG. 4 using the serial number determined in step S305. The control unit 101 then acquires the correction parameter by identifying the correction data file.

In step S307, the control unit 101 performs radiographing. In general, the operator pushes the irradiation button or steps on a pedal to instruct the radiation generation apparatus to start irradiating the subject with radiation. The radiation generation apparatus then generates radiation, and the sensor receives and collects as the image data the radiation transmitted through the subject.

In step S308, the control unit 101 performs image processing including the correction process on the image data collected in step S307. The image processing performed in step 308 uses the correction parameter determined in step S306. Other image processing uses the image processing parameter determined in step 304.

In step S309, the control unit 101 displays on the display unit 105 the image on which image processing has been performed in step S308 (i.e., a display control step). The structure of the data according to the present exemplary embodiment will be described below. FIG. 5 illustrates a logical structure of each data according to the present exemplary embodiment.

Referring to FIG. 5, a radiographing site 501 acts as a label and is used to determine various conditions to be employed when the operator performs radiographing. More specifically, the radiographing site 501 is not only limited to indicating the site and may also include orientation, such as "front chest" and "lateral aspect of chest". Further, the radiographing site may be freely defined to be as "infant" or "operator A", other than the site and the orientation. Such information can be created by the user as desired.

A radiographing posture 503 of the subject is the identification information used to switch between the table and the stand for attaching the sensor unit. For example, the radiographing posture "stand 40EG" illustrated in FIG. 5 indicates the radiographing posture in which the sensor unit of a model 40EG is attached to the stand type pedestal. In such a case, only the information about the model of the sensor to be used in the radiographing posture is identified, and the individual sensor is not identified.

A radiographing procedure 502 is the information expressed by a combination of the radiographing site 501 and the radiographing posture 503. The radiographing procedure "front chest standing" illustrated in FIG. 5 indicates that "front chest" is selected as the radiographing site and "stand 40EG" as the radiographing posture. In the actual system, the radiographing procedure is expressed on the screen as a button which is then selected by the operator.

Sensor information 504 is information indicating each sensor, which is managed with the model of the sensor unit and the serial number assigned to each sensor. The correction parameter is managed for each of the combination of the sensor information 504 and the radiographing posture 503.

Referring to FIG. 5, the sensor unit "40EG S/N22446688" corresponding to "stand 40EG" is already corrected. Further, since calibration is not performed on the sensor unit "40EG 98765432", there is no correction parameter.

A radiographing distance and various conditions of the correction parameter employed when radiographing is performed are different for each radiographing posture. The correction parameter is thus managed for each radiographing posture and sensor unit. However, if only the sensor unit itself is to be corrected, the correction parameter may be managed for each sensor unit. In such a case, the correction parameter is determined based on the sensor to be used regardless of the radiographing posture.

The management table illustrated in FIG. 4 is an example in which the correction parameter is managed for each sensor unit. However, if the correction parameter is to be managed for each combination of the sensor unit and the radiographing posture, the radiographing posture is included in the management table illustrated in FIG. 4.

Parameters 506 indicate the image processing parameters and the radiographic imaging parameters, which are defined for each radiographing procedure. More specifically, the image processing parameter and the radiographic imaging parameter are determined based on the radiographing procedure selected by the operator or the system.

Figure 6:
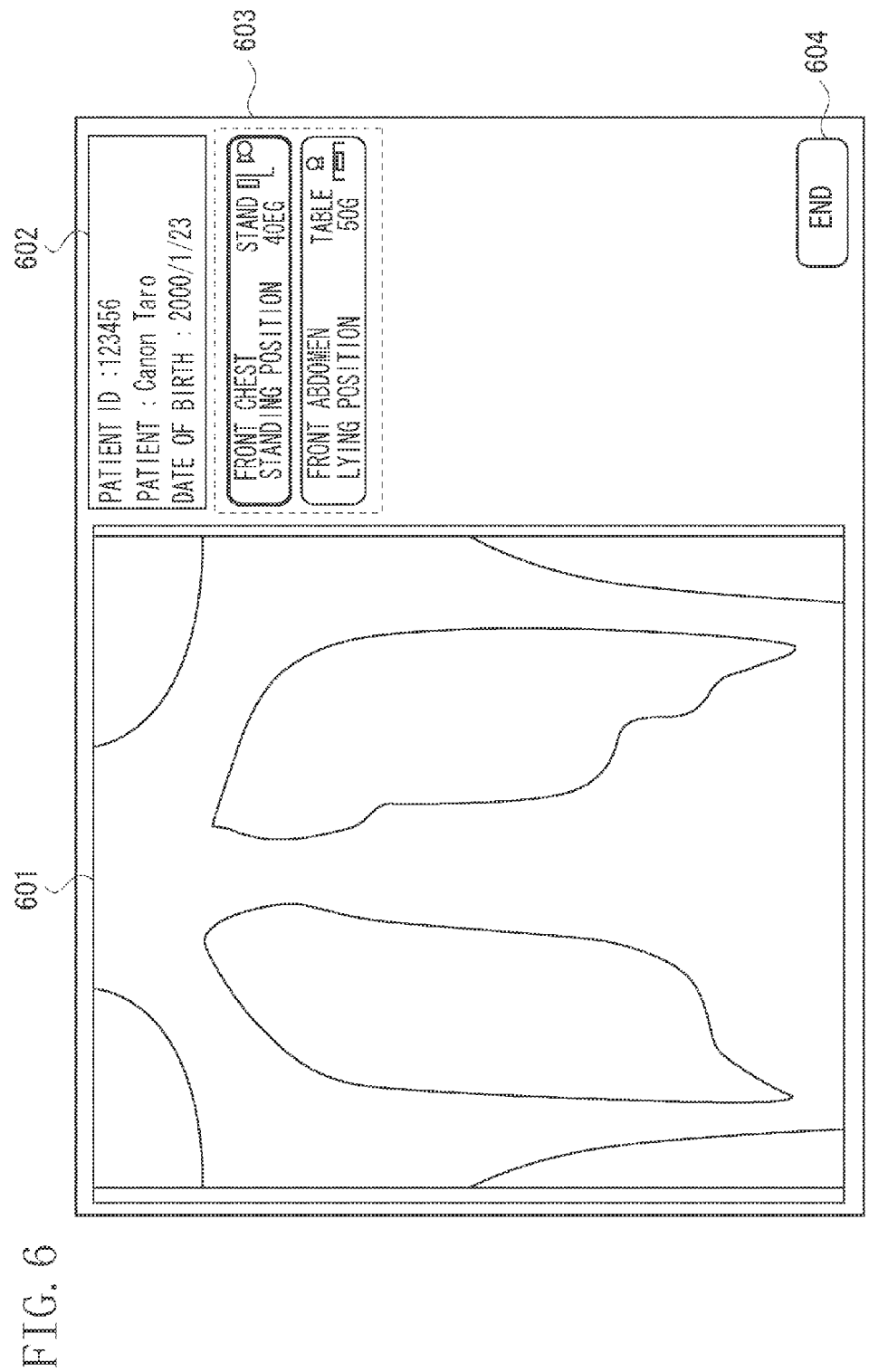
FIG. 6 illustrates an example of a graphical user interface (GUI) according to the first exemplary embodiment of the present invention.

FIG. 6 illustrates an example of a GUI used in performing radiographing according to the present exemplary embodiment. Referring to FIG. 6, an image display area 601 displays the radiographed image. An area 602 displays information about the patient who is being radiographed.

A radiographing procedure button 603 corresponds to the information of the radiographing procedure 502 illustrated in FIG. 5. In the example illustrated in FIG. 6, the operator has selected the button in which "front chest standing stand 40EG" is displayed. This indicates that "front chest" is internally designated as the radiographing site and "stand 40EG" as the radiographing posture.

FIG. 6 illustrates the screen directly after radiographing is performed. The screen displays an image on which processing is performed according to the image processing parameter and the correction parameter that are determined based on the selected "front chest standing stand 40EG" procedure. A button 604 is used for ending the examination.

A method for determining the sensor unit which is actually used when the operator selects the radiographing procedure will be described below. When the operator selects the radiographing procedure in FIG. 6, the radiographing posture to be initially used is also specified. In the case illustrated in FIG. 6, "stand 40EG" is specified as the radiographing posture.

The sensor unit "s/n: 98765432" and the sensor unit "s/n: 22446688" are previously registered to the radiographing posture "stand 40EG". In other words, when "stand 40EG" is specified as the radiographing posture, candidates for connection are narrowed down to the above-described two sensor units.

The radiographic imaging system then refers to the management table illustrated in FIG. 4. Since the table manages the connection status of each sensor as described above, the radiographic imaging system refers to the information about the two sensors, which are connection candidates, and confirms the connection status of each sensor.

In the example of the management table illustrated in FIG. 4, the sensor unit "s/n: 98765432" is in an off-line state, and the sensor unit "s/n: 22446688" is in an online state. The sensor unit "s/n: 22446688" is thus determined as the sensor unit to be used in performing radiographing.

Since the correction parameter to be used can be determined at the same time, the collected radiographic image is corrected using the determined correction parameter. A case where two sensors are both indicated as in the online states in the sensor management table illustrated in FIG. 4 does not occur if the sensors are a general wired connection type sensor units.

Since the two sensor units cannot be physically attached to a bucky unit of one stand, the above-described case does not occur. As a result, one sensor unit is generally specified to be usable with respect to one radiographing posture.

As described above, according to the present exemplary embodiment, the operator can determine, by only selecting the radiographing procedure, the sensor unit of the system for performing radiographing by attaching the sensor unit to the various pedestals. Further, the appropriate correction parameter and the image processing parameter are determined at the same time as the sensor unit is determined. The operator can thus perform radiographing without consideration of the sensor unit to be used, so that the user-friendliness is improved.

Each of the processes according to the present exemplary embodiment may be realized by a processing apparatus (such as the CPU or a processor) executing software (i.e., a program code) acquired from a network or various storage media.

According to the first exemplary embodiment, one sensor unit is generally specified to be usable with respect to the designated radiographing posture in the radiographic imaging system. However, in a case of a wireless type sensor unit, this is not necessarily held true. For example, when a plurality of sensor information is registered with respect to one radiographing posture in the management table illustrated in FIG. 4, the connection statuses of the plurality of sensors may become online at the same time.

Further, if one sensor unit is previously registered to be used in different radiographing postures, the radiographing posture with which the sensor unit is to be used becomes unclear.

According to the second exemplary embodiment, when the connection of the wireless sensor unit is detected, the radiographing posture to which the sensor unit is to be assigned is confirmed. The present exemplary embodiment assumes a case where a plurality of sensor units is registered to a radiographing posture that uses a wireless connection type sensor. The present exemplary embodiment also assumes a case where there is a plurality of radiographing postures that uses the wireless connection type sensor, and there is one sensor unit or a plurality of sensor units.

Figure 7:
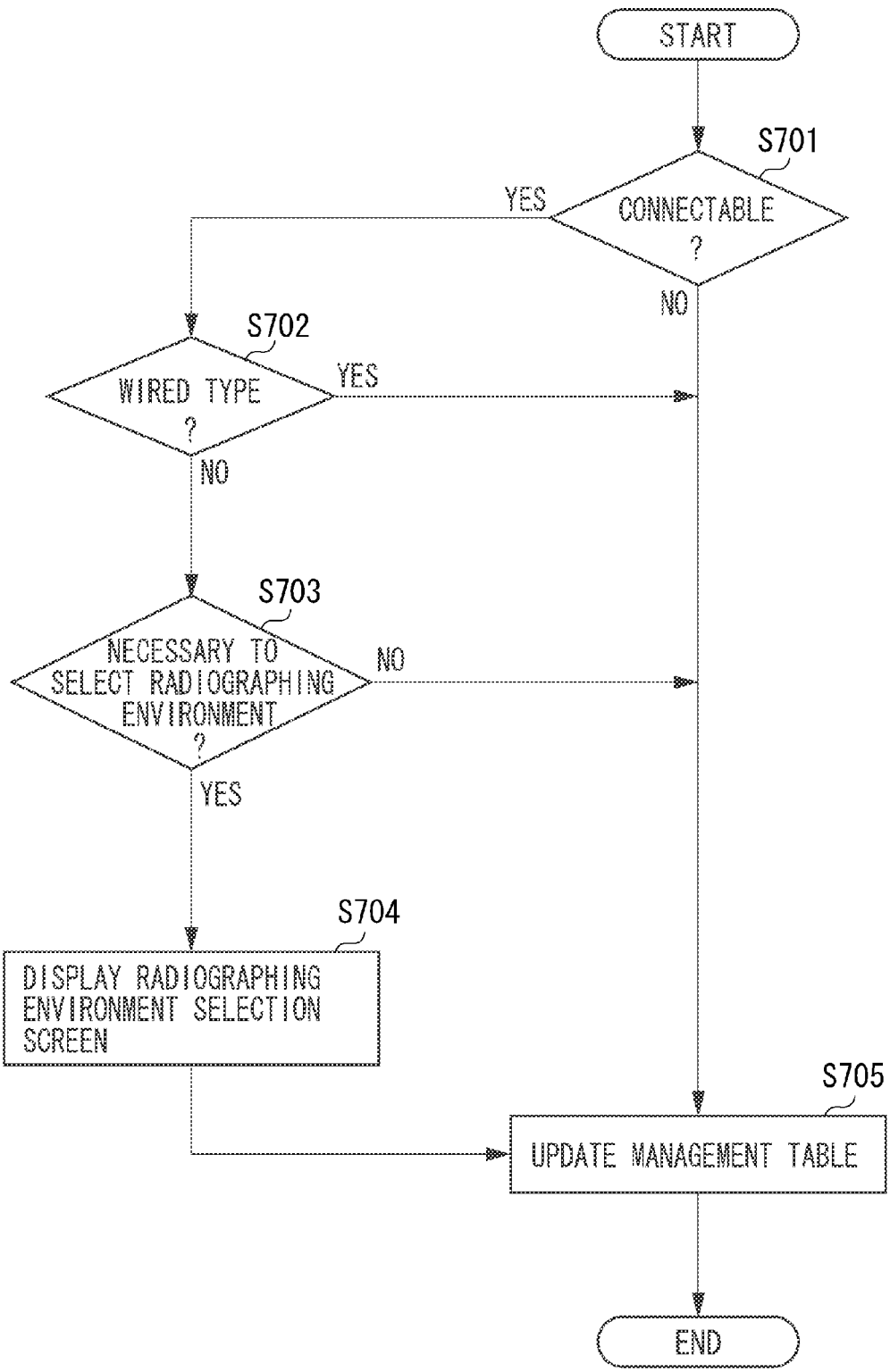
FIG. 7 illustrates a flowchart of a process according to a second exemplary embodiment of the present invention.

FIG. 7 is a flowchart illustrating in detail the process performed in step S301 illustrated in FIG. 3 (i.e., the sensor state confirmation step). The process flow according to the present exemplary embodiment will be described below with reference to FIG. 7.

In step S701, the control unit 101 confirms the connection with the sensor unit. If it is determined that the sensor unit is connectable (YES in step S701), the process proceeds to step S702. On the other hand, if it is determined that the sensor unit is not connectable (NO in step S701), the process proceeds to step S705.

In step S702, the control unit 101 confirms the connection type of the sensor unit. The control unit 101 may confirm the information of the sensor model which is previously registered, or acquire the connection type from the sensor unit by actually communicating with the sensor unit. According to the present process, the control unit 101 acquires the serial number from the sensor unit. If it is then determined that the connection type is the wired connection (YES in step S702), the process proceeds to step S705. If it is determined that the connection type is wireless connection (NO in step S702), the process proceeds to step S703.

In step S703, the control unit 101 confirms the radiographing postures registered to the system. More specifically, the control unit 101 confirms whether the registered radiographing posture information uses the same type of sensor unit as the sensor unit whose connection is currently being confirmed.

If there is a plurality of radiographing postures that uses the same type of sensor unit (YES in step S703), the control unit 101 determines that it is necessary to select the radiographing posture, and the process proceeds to step S704. On the other hand, if only one radiographing posture that uses the same type of sensor unit is registered to the system (NO in step S703), the control unit 101 determines that it is not necessary to select the radiographing posture. The process then proceeds to step S705.

In step S704, the control unit 101 displays the screen for causing the operator to select the radiographing posture to be used with the sensor unit that is detected to be connectable.

The operator is thus caused to determine the radiographing posture. When the operator determines the radiographing posture, the process proceeds to step S705. In step S705, the control unit 101 updates the management table.

Figure 8:
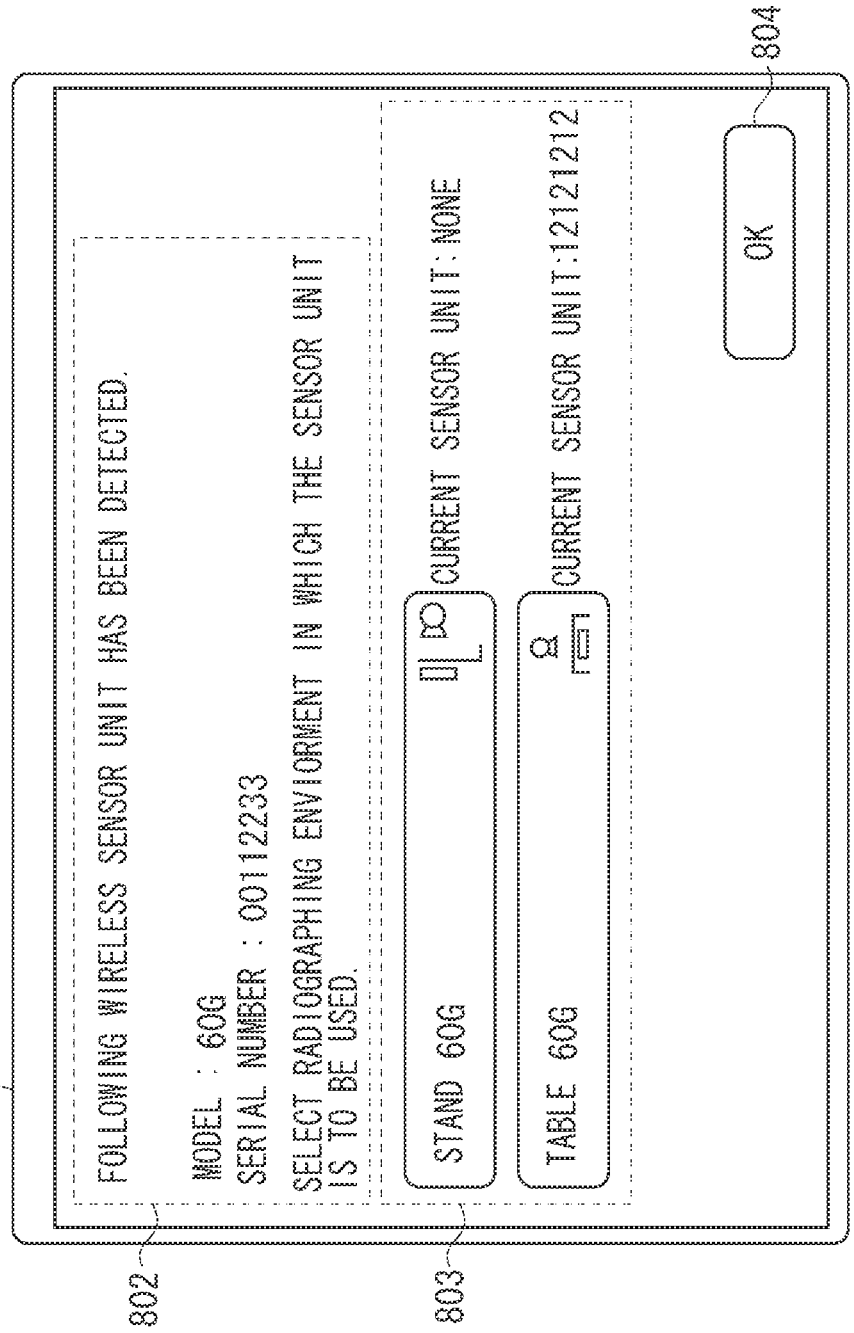
FIG. 8 illustrates an example of a GUI according to the second exemplary embodiment of the present invention.

FIG. 8 illustrates an example of the screen displayed in step S704 illustrated in FIG. 7 (i.e., a radiographing posture selection screen display step). Referring to FIG. 8, a radiographing posture selection screen 801 is displayed in step S704. An area 802 displays an operation instruction and the sensor unit information to the operator, and displays the information about the wireless connection type sensor detected in the sensor connection confirmation process. The example illustrated in FIG. 8 indicates that the sensor unit of model 60G and serial number 00112233 has become online and is detected.

Buttons 803 are used by the operator to select the radiographing posture. The example illustrated in FIG. 8 indicates that "stand 60G" and "table 60G" are previously registered as the radiographing posture using the sensor unit of type 60G. Further, there is no sensor unit that is currently assigned to "stand 60G", and the sensor unit whose serial number is 12121212 is assigned to "table 60G".

Upon the operator clicking the radiographing posture, the radiographing posture corresponding to the clicked button is set to be usable with respect to the detected sensor. If the operator selects a radiographing posture to which a sensor is previously assigned to, the setting is overwritten, and the assignment is updated to a new sensor unit. A button 804 is pressed to complete the setting.

The operator may remove the sensor unit, which is used by being assigned to the radiographing posture "stand 60G", from the bucky unit of the stand type pedestal, and may attach the sensor unit to the bucky unit of the table type pedestal. The operator may move the sensor unit while the status of the connection to the system remains online.

However, since the change in the connection status cannot be detected in the above-described case, the process illustrated in FIG. 7 cannot be performed. As a result, the screen for assigning the radiographing posture to the sensor unit cannot be displayed to the operator.

To solve such a problem, if the wireless connection type sensor unit can be registered to a plurality of radiographing postures in the present radiographic imaging system, a screen (not illustrated) is provided so that the operator can change the assignment. The operator can thus change the assignment of the sensor unit to the radiographing posture at any time.

In the a exemplary embodiment, the process for determining the radiographing procedure before the operator starts performing the examination will be described. The connection types of the sensors in the radiographic imaging system are a wired fixed type, a wired attachable/detachable type, and the wireless type. Each of the connection types will be described below.

In the case of the wired fixed type connection, the control unit and the sensor unit are fixedly connected via a cable. In such a case, it is necessary for the sensor unit to be activated before the system in the control unit is activated. If the sensor unit is activated after activating the control unit, the control unit cannot detect the sensor unit.

In contrast, in the case of the wired attachable/detachable type connection, there is no restriction on the order of activating the sensor and the control unit. Further, the cable is attachable to and detachable from the sensor unit main body, and the control unit can detect the attached and detached states of the cable.

In the case of the wireless type connection, the sensor unit and the control unit are connected by a cable-less connection, i.e., electrically connected by wireless signals. The wired attachable/detachable type and the wireless type sensors are freely movable even when performing radiographing. However, the wired fixed type sensor unit is basically not movable.

If the wired fixed connection type sensor unit is then determined as off-line in the management table illustrated in FIG. 4, the sensor is not determined as valid unless the system is re-activated after activating the sensor unit.

In the radiophotographic imaging system according to the present invention, the operator selects as necessary (or the system automatically selects) the radiographing procedure, which is aligned on the right side of the imaging screen as illustrated in FIG. 6. Radiographing is thus sequentially performed.

There is a process for determining the radiographing procedure aligned on the right side of the imaging screen as illustrated in FIG. 6 in the radiophotographic imaging system (whose description is omitted in the first exemplary embodiment). In such a process, the operator selects and adds the radiographing procedure before starting the examination, so that the operator previously designates the radiographing to be performed.

Figure 9:
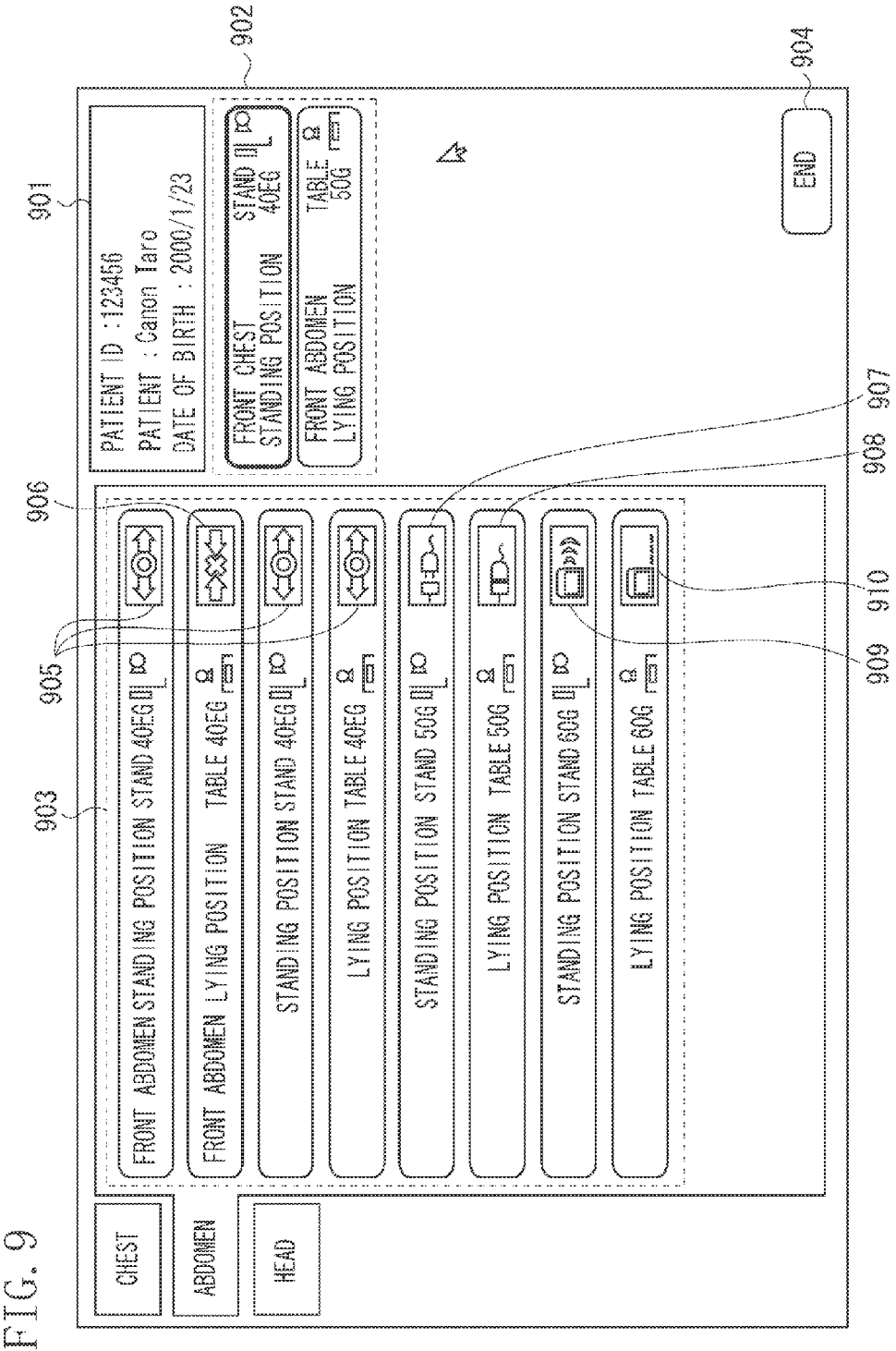
FIG. 9 illustrates an example of a GUI according to a third exemplary embodiment of the present invention.

FIG. 9 illustrates an example of a screen for selecting the radiographing procedure before starting the examination. Referring to FIG. 9, an area 901 displays the name of the patient whose examination will be started from now. A radiographing procedure list 902 displays the procedures to be performed in the examination to be started from now.

Upon the operator clicking a radiographing procedure button 903, the radiographing procedure is added to the radiographing procedure list 902 on the right side of the screen. When the operator clicks a start button 904, the examination is started, and the screen shifts to the imaging screen illustrated in FIG. 6.

In FIG. 9, six radiographing postures are indicated, i.e., "stand 40EG", "table 40EG", "stand 50G", "table 50G", "stand 60G", and "table 60G". 40EG indicates the wired fixed type, 50G the wired attachable/detachable type, 60G the wireless type sensor unit as illustrated in FIG. 4.

For example, the operator selects on the screen illustrated in FIG. 9 the radiographing posture "front abdomen lying position table 40EG" which uses the wired fixed type sensor unit. If the communication with the sensor unit cannot be established when starting the examination, radiographing cannot be performed when the radiographing procedure is selected on the imaging screen.

In such a case, it is necessary for the operator to turn on the sensor unit and reactivate the system, and the patient is required to wait during the process. To prevent such a problem, the selection of the radiographing procedure that uses the wired fixed connection type sensor is limited to only when such radiographing procedure is in the usable state. Preparation is thus performed before starting the examination to assure that radiographing is performed.

On the other hand, if the wired attachable/detachable type or the wireless type sensor is assigned to the radiographing procedure, the sensor can be freely moved after starting the examination. The radiographing procedure can thus be selected even when the connection cannot be established before starting the examination.

As described above, it is desirable to control the selectability and display form of the radiographing procedure according to the connection status before starting examination, for each connection type of the sensor unit registered with respect to the radiographing posture. Display areas 905, 906, 907, 908, 909, and 910 are the radiographing posture connection status display areas that indicate the information for performing such control and indicate the connectable state of the radiographing posture associated with each of the radiographing procedure.

The display area 905 indicates a state in which the connection is established for the wired fixed connection type sensor, and the radiographing procedure button is also displayed in a selectable state. On the other hand, the display area 906 displays a state in which the wired fixed connection type sensor is not connected. Since the sensor is the wired fixed connection type, the radiographing procedure button itself becomes invalid and is not in the selectable state. The display area 907 displays a state in which the wired attachable/detachable type sensor is not connected.

The display area 908 displays a state in which at least one wired attachable/detachable type sensor unit is attached and is in a communicable state. In any case, the sensor unit can be attached and exchanged after starting the examination, so that the radiographing procedure button is displayed in the selectable state even when the sensor is not connected.

The display area 909 indicates a state in which at least one wireless connection type sensor unit is in the communicable state. The display area 910 indicates that there is no wireless connection type sensor unit in which the connection is established. Even in such a case, the communication can be established by causing the system to recognize the sensor unit after starting the examination. The radiographing procedure button is thus displayed in the selectable state.

As described above, the radiographic imaging system according to the present exemplary embodiment can prevent the operator from selecting the radiographing procedure by which radiographing cannot be performed before the operator starts the examination. This is realized by changing the display form of the radiographing procedure according to the connection type and the connection status of the sensor unit to be used in the radiographing posture associated with the radiographing procedure. As a result, it reduces cases where the operator selects the radiographing procedure by which radiographing cannot be performed after starting the examination, so that restarting of the examination can be reduced.

Aspects of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable medium). In such a case, the system or apparatus, and the recording medium where the program is stored, are included as being within the scope of the present invention.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-202680 filed Sep. 2, 2009, which is hereby incorporated by reference herein in its entirety.

What is claimed is:

1. A radiographic imaging apparatus that is connectable to a plurality of wireless radiation sensors, comprising:

an information acquisition unit configured to acquire a radiographing site of a subject radiographed by at least one of the plurality of wireless radiation sensors;
a sensor drive status management unit configured to manage drive statuses of the plurality of wireless radiation sensors;
a sensor connection status detecting unit configured to detect a sensor connection status of a connection between the radiographic imaging apparatus and the plurality of wireless radiation sensors; and
a sensor selection unit configured to select a wireless radiation sensor to be used in performing radiographing from the plurality of wireless radiation sensors connected to the radiographic imaging apparatus by wireless connection, based on the acquired radiographing site and drive statuses of the plurality of wireless radiation sensors when the sensor connection status is detected by the sensor connection status detecting unit,
wherein, when there is a plurality of radiographing postures in the same type of wireless radiation sensors, the sensor selection unit selects the wireless radiation sensor from the same type of wireless radiation sensors by selecting the radiographing posture from the plurality of radiographing postures.

2. The radiographic imaging apparatus according to claim 1, further comprising:
a correction parameter management unit configured to manage the plurality of wireless radiation sensors associated with correction parameters; and
a correction parameter selection unit configured to select from the correction parameters managed by the correction parameter management unit a correction parameter for the wireless radiation sensor to be used in performing the radiographing, the correction parameter selection unit selecting the correction parameter based on the wireless radiation sensor selected by the sensor selection unit.

3. The radiographic imaging apparatus according to claim 1, further comprising a display control unit configured to display information about a radiographing site and the radiographing posture of the subject as buttons to be selectable by an operator,
wherein the information acquisition unit acquires information about the radiographing site and the radiographing posture of the subject based on a selection of a button by the operator.

4. The radiographic imaging apparatus according to claim 3, wherein the display control unit restricts selection of the buttons by the operator according to drive statuses of the plurality of wireless radiation sensors.

5. The image processing apparatus according to claim 1, wherein the sensor selection unit displays candidates for the wireless radiation sensor to be used in performing radiographing, based on the acquired radiographing site and the drive statuses of the plurality of wireless radiation sensors, and selects the wireless radiation sensor to be used in performing radiographing according to a selection instruction from an operator.

6. A method for controlling a radiographic imaging apparatus that is connectable to a plurality of wireless radiation sensors, the method comprising:
acquiring a radiographing site of a subject radiographed by at least one of the plurality of wireless radiation sensors;
managing drive statuses of the plurality of wireless radiation sensors;
detecting a sensor connection status of a connection between the radiographic imaging apparatus and the plurality of wireless radiation sensors; and
selecting a wireless radiation sensor to be used in performing radiographing from the plurality of wireless radiation sensors connected to the radiographic imaging apparatus by wireless connection, wherein the selecting of the wireless radiation sensor to be used in performing radiographing is based on the acquired radiographing site and drive statuses of the plurality of wireless radiation sensors when the sensor connection status is detected by the detecting step,
wherein, when there is a plurality of radiographing postures in the same type of wireless radiation sensors, the selecting includes selecting the wireless radiation sensor from the same type of wireless radiation sensors by selecting the radiographing posture from the plurality of radiographing postures.

7. A non-transitory computer-readable storage medium storing a computer program for causing a computer to control a radiographic imaging apparatus that is connectable to a plurality of wireless radiation sensors, the program including computer-processing steps comprising:
an information acquisition step executed to acquire a radiographing site of a subject radiographed by at least one of the plurality of wireless radiation sensors;
a sensor drive status management step executed to manage drive statuses of the plurality of wireless radiation sensors;
a sensor connection status detecting step executed to detect a sensor connection status of a connection between the radiographic imaging apparatus and the plurality of wireless radiation sensors; and
a sensor selection step executed to select a wireless radiation sensor to be used in performing radiographing from the plurality of wireless radiation sensors connected to the radiographic imaging apparatus by wireless connection, based on the acquired radiographing site and drive statuses of the plurality of wireless radiation sensors when the sensor connection status is detected by the sensor connection status detecting step,
wherein, when there is a plurality of radiographing postures in the same type of wireless radiation sensors, the sensor selection step selects the wireless radiation sensor from the same type of wireless radiation sensors by selecting the radiographing posture from the plurality of radiographing postures.

8. A radiographic imaging apparatus that is connectable to a plurality of radiation sensors comprising:
an information acquisition unit configured to acquire a radiographing posture of a subject radiographed by at least one of the plurality of radiation sensors;
a sensor drive status management unit configured to manage drive statuses of the plurality of radiation sensors;
a sensor selection unit configured to select a radiation sensor to be used in performing radiographing from the plurality of radiation sensors, the sensor selection unit selecting the radiation sensor to be used in performing radiographing based on the acquired radiographing posture and drive statuses of the plurality of radiation sensors, wherein, when there is a plurality of radiographing postures in the same type of wireless radiation sensors, the sensor selection unit selects the wireless radiation sensor from the same type of wireless radiation sensors by selecting the radiographing posture from the plurality of radiographing postures;

a correction parameter management unit configured to manage the plurality of radiation sensors associated with correction parameters; and a correction parameter selection unit configured to select from the correction parameters managed by the correction parameter management unit a correction parameter for the radiation sensor to be used in performing the radiographing, based on the radiation sensor selected by the sensor selection unit.

9. A radiographic imaging apparatus that is connectable to a plurality of wireless radiation sensors, comprising:

an information acquisition unit configured to acquire a radiographing region and a radiographing posture of a subject;

a sensor drive status management unit configured to manage drive statuses of the plurality of wireless radiation sensors;

a sensor connection status detecting unit configured to detect a sensor connection status of a connection between the radiographic imaging apparatus and the plurality of wireless radiation sensors; and a sensor selection unit configured to select a wireless radiation sensor to be used in performing radiographing from the plurality of wireless radiation sensors connected to the radiographic imaging apparatus by wireless connection, based on the acquired radiographing region and radiographing posture and drive statuses of the plurality of wireless radiation sensors when the sensor connection status is detected by the sensor connection status detecting unit, wherein, when there is a plurality of radiographing postures in the same type of wireless radiation sensors, the sensor selection unit selects the wireless radiation sensor from the same type of wireless radiation sensors by selecting the radiographing posture from the plurality of radiographing postures.

10. The radiographic imaging apparatus according to claim 9, further comprising a display control unit configured to display information about the radiographing region and the radiographing posture of the subject as buttons to be selectable by the an operator.

11. The radiographic imaging apparatus according to claim 9, wherein the information acquisition unit acquires information about the radiographing region or the radiographing posture of the subject based on a selection of a button by an operator.

12. The radiographic imaging apparatus according to claim 10, wherein the display control unit restricts selection of the buttons by the operator according to drive statuses of the plurality of wireless radiation sensors.

13. The image processing apparatus according to claim 9, wherein the sensor selection unit displays candidates for the wireless radiation sensor to be used in performing radiographing, based on the acquired radiographing region and radiographing posture and the drive statuses of the plurality of wireless radiation sensors, and selects the wireless radiation sensor to be used in performing radiographing according to a selection instruction from an operator.

14. A method for controlling a radiographic imaging apparatus that is connectable to a plurality of wireless radiation sensors, the method comprising:

acquiring a radiographing region and a radiographing posture of a subject;

managing drive statuses of the plurality of wireless radiation sensors;

detecting a sensor connection status of a connection between the radiographic imaging apparatus and the plurality of wireless radiation sensors; and selecting a wireless radiation sensor to be used in performing radiographing from the plurality of wireless radiation sensors connected to the radiographic imaging apparatus by wireless connection, wherein the selecting of the wireless radiation sensor to be used in performing radiographing is based on the acquired radiographing region and radiographing posture and drive statuses of the plurality of wireless radiation sensors when the sensor connection status is detected by the detecting step, wherein, when there is a plurality of radiographing postures in the same type of wireless radiation sensors, the selecting includes selecting the wireless radiation sensor from the same type of wireless radiation sensors by selecting the radiographing posture from the plurality of radiographing postures.

15. A non-transitory computer-readable storage medium storing a computer program for causing a computer to control a radiographic imaging apparatus that is connectable to a plurality of wireless radiation sensors, the program including computer-processing steps comprising:

an information acquisition step executed to acquire a radiographing region and a radiographing posture of a subject;

a sensor drive status management step executed to manage drive statuses of the plurality of wireless radiation sensors;

a sensor connection status detecting step executed to detect a sensor connection status of a connection between the radiographic imaging apparatus and the plurality of wireless radiation sensors; and a sensor selection step executed to select a wireless radiation sensor to be used in performing radiographing from the plurality of wireless radiation sensors connected to the radiographic imaging apparatus by wireless connection, based on the acquired radiographing region and radiographing posture and drive statuses of the plurality of wireless radiation sensors when the sensor connection status is detected by the sensor connection status detecting unit, wherein, when there is a plurality of radiographing postures in the same type of wireless radiation sensors, the sensor selection step selects the wireless radiation sensor from the same type of wireless radiation sensors by selecting the radiographing posture from the plurality of radiographing postures.

16. A radiographic imaging apparatus that is connectable to a plurality of wireless radiation sensors, comprising:

a detecting unit configured to detect connection statuses of the plurality of wireless radiation sensors;

a sensor status management unit configured to manage a status management table indicating connection statuses of the plurality of wireless radiation sensors by updating, if connections of the plurality of wireless radiation sensors are detected, connection statuses of the plurality of wireless radiation sensors;

an information acquisition unit configured to acquire information about a radiographing site of a subject; and a sensor selection unit configured to select a wireless radiation sensor to be used in performing radiographing from the plurality of wireless radiation sensors whose connections are detected, based on the acquired information about the radiographing site of the subject and connection statuses of the plurality of wireless radiation sensors, wherein, when there is a plurality of radiographing postures in the same type of wireless radiation sensors, the sensor selection unit selects the wireless radiation sensor from the same type of wireless radiation sensors by selecting the radiographing posture from the plurality of radiographing postures.

17. A method for controlling a radiographic imaging apparatus that is connectable to a plurality of wireless radiation sensors, the method comprising:

detecting connection statuses of the plurality of wireless radiation sensors;

managing a status management table indicating connection statuses of the plurality of wireless radiation sensors by updating, if connections of the plurality of wireless radiation sensors are detected, connection statuses of the plurality of wireless radiation sensors;

acquiring information about a radiographing site of a subject; and selecting a wireless radiation sensor to be used in performing radiographing from the plurality of wireless radiation sensors whose connections are detected, based on the acquired information about the radiographing site of the subject and connection statuses of the plurality of wireless radiation sensors, wherein, when there is a plurality of radiographing postures in the same type of wireless radiation sensors, the selecting includes selecting the wireless radiation sensor from the same type of wireless radiation sensors by selecting the radiographing posture from the plurality of radiographing postures.

18. A non-transitory computer-readable storage medium storing a computer program for causing a computer to control a radiographic imaging apparatus that is connectable to a plurality of wireless radiation sensors, the program including computer-processing steps comprising:

a detecting step executed to detect connection statuses of the plurality of wireless radiation sensors;

a sensor status management step executed to manage a status management table indicating connection statuses of the plurality of wireless radiation sensors by updating, if connections of the plurality of wireless radiation sensors are detected, connection statuses of the plurality of wireless radiation sensors;

an information acquisition step executed to acquire information about a radiographing site of a subject; and a sensor selection step executed to select a wireless radiation sensor to be used in performing radiographing from the plurality of wireless radiation sensors whose connections are detected, based on the acquired information about the radiographing site of the subject and connection statuses of the plurality of wireless radiation sensors, wherein, when there is a plurality of radiographing postures in the same type of wireless radiation sensors, the sensor selection steps selects the wireless radiation sensor from the same type of wireless radiation sensors by selecting the radiographing posture from the plurality of radiographing postures.

* * * * *